US006120835A

United States Patent [19]
Perdieu

[11] Patent Number: 6,120,835
[45] Date of Patent: Sep. 19, 2000

[54] PROCESS FOR MANUFACTURE OF THICK FILM HYDROGEN SENSORS

[75] Inventor: Louisa H. Perdieu, Overland Park, Kans.

[73] Assignee: Honeywell International Inc., Morris Township, N.J.

[21] Appl. No.: 09/351,878

[22] Filed: Jul. 13, 1999

Related U.S. Application Data

[60] Provisional application No. 60/103,071, Oct. 5, 1998, abandoned.

[51] Int. Cl.[7] .......................................................... B05D 5/12
[52] U.S. Cl. ............................ 427/125; 427/102; 427/379
[58] Field of Search ..................................... 427/123, 125, 427/379, 380, 383.1, 409, 102; 338/34

[56] References Cited

U.S. PATENT DOCUMENTS

| | | |
|---|---|---|
| 3,559,457 | 2/1971 | Collins . |
| 4,624,137 | 11/1986 | Johnson et al. . |
| 4,908,118 | 3/1990 | Ammende et al. . |
| 4,931,851 | 6/1990 | Sibbald et al. . |
| 4,976,991 | 12/1990 | Ammende et al. . |
| 5,338,708 | 8/1994 | Felten . |
| 5,367,283 | 11/1994 | Lauf et al. . |
| 5,451,920 | 9/1995 | Hoffheins et al. ......................... 338/34 |

OTHER PUBLICATIONS

B.S. Hoffheins, A Thick–film Hydrogen Sensor, proceedings of Int'l Symposium on Hybrid Electronics, No month Available 1994 proceedings, pp. 542–547.
P.J. Shaver, Bimetal Strip Hydrogen Gas Detectors, The Review of Scientific Instruments, vol. 40, No. 7, Jul. 1969, pp. 901–905.
P.A. Michaels, "Design, Development and Phototype Fabrication of an Area Hydrogen Detector (Apr. 5, 1963–Apr. 4, 1964)", submitted to George C. Marshall Space Flight Center, Huntsville, Ala., by Bendix Corp., dated Sep. 1964.
M.A. Butler, Hydrogen Sensing With Palladium–coated Optical Fibers, J. Appl. Physics 64(7), Oct. 1, 1968.

*Primary Examiner*—Brian K. Talbot
*Attorney, Agent, or Firm*—Hovey, Williams, Timmons & Collins

[57] ABSTRACT

A thick film process for producing hydrogen sensors capable of sensing down to a one percent concentration of hydrogen in carrier gasses such as argon, nitrogen, and air. The sensor is also suitable to detect hydrogen gas while immersed in transformer oil. The sensor includes a palladium resistance network thick film printed on a substrate, a portion of which network is coated with a protective hydrogen barrier. The process utilizes a sequence of printing of the requisite materials on a non-conductive substrate with firing temperatures at each step which are less than or equal to the temperature at the previous step.

12 Claims, 3 Drawing Sheets

PROCESS FOR MANUFACTURE OF THICK FILM HYDROGEN SENSORS

The U.S. Government has rights in this invention pursuant to contract DE-AC04-76-DP00613 with the United States Department of Energy.

This patent is entitled to priority pursuant to Provisional U.S. patent application 60/103,071 filed Oct. 5, 1998 now abandoned.

BACKGROUND OF THE INVENTION

This invention generally relates to the manufacture of hydrogen sensors and, more particularly, to the use of thick film printing processes to print palladium paste and other conductive and protective layers onto a substrate to manufacture resistance-type hydrogen sensors. This invention also includes the product of the manufacturing process.

Various types of electronic assemblies, manufacturing processes, machines and other devices utilize, produce, or are harmed by the presence of hydrogen gas. Therefore, a number of sensing devices have been developed to detect and measure the presence of hydrogen. One desirable characteristic of such sensing devices is to detect hydrogen at low concentrations, around a 1% to about 3% hydrogen in the atmosphere. Sensing at low concentrations is desirable first to minimize the harmful effects of hydrogen (i.e., metal embrittlement, etc.) and second, to provide better anticipation to avoid explosive mixtures (hydrogen reaches an explosive concentration at about 4%).

A variety of techniques to sense the presence of hydrogen have been developed over the years including various methods discussed in U.S. Pat. No. 5,451,920 (referred to herein as the "'920 patent") which is incorporated herein by reference. In particular, thin and thick film hydrogen sensors have been developed which utilize palladium (Pd) metal films to form a resistance network. Palladium metal changes in its electrical resistance characteristics as it is exposed to hydrogen. Thus, changes in the electrical characteristics of such a network can be utilized to sense the presence of hydrogen.

Typically, such sensing networks are set up to form a Wheatstone Bridge or the like wherein one or two of the four legs of the bridge are formed from palladium which is exposed to the gas to be sensed and two legs of the bridge are palladium which has been encapsulated so as to protect those legs from exposure to such gas. Additional elements are added to the bridge to form balancing resistors so that the bridge preferably may be balanced in all four quadrants when no hydrogen is being detected.

Existing hydrogen sensors made by thick film processes such as are discussed in the '920 patent have several limitations. Perhaps the most crucial is that these sensors have a tendency to be inaccurate and not reliably sense hydrogen at concentrations below a 4% concentration level. Moreover, the sensors have a tendency to drift or degrade with time. Some of these characteristics appear related to problems experienced in the process of applying a passivation layer, i.e., the process of encapsulating portions of the palladium to prevent hydrogen from reaching portions of the network. Another notable limitation of processes such as described in the '920 patent is that such processes historically produce relatively low yields of useable sensors and the process repeatability is lacking, due apparently to problems in reliably achieving adherence of various portions of the thick film network to the substrate involved.

SUMMARY OF THE INVENTION

Accordingly, is an object of the present invention to provide a new and improved system for thick film production of palladium hydrogen sensing elements with enhanced accuracy and repeatability. It is a further object of this invention that the sensors produced by the present invention process are suitable to detect hydrogen concentrations of about 1% hydrogen in air. It is a further object of this invention that the yield, accuracy, and repeatability of the process are enhanced so that the resulting dependability of the sensors involved is maxi maximized.

The present invention process to form sensors of the present invention is a thick film process comprising printing a sensor conductor paste comprised of palladium in a suitable binder and carrier onto an essentially inert, electrically nonconductive substrate in a pattern to form at least two electrical networks, firing the substrate and sensor conductor paste at a first peak temperature and for a first duration, which temperature and duration are sufficient to firmly adhere said electrical network to said substrate, printing a passivating material which is essentially inert, electrically insulating, and hydrogen impermeable onto at least one, but less than all of the electrical networks, and firing the substrate and passivating material at a second peak temperature and for a second duration, which second temperature and second duration are sufficient to firmly adhere the passivating material to said electrical networks, without forming bubbles, voids or cracks, the second temperature being less than or equal to said first temperature.

DETAILED DESCRIPTION AND PREFERRED EMBODIMENTS

Figure 1:
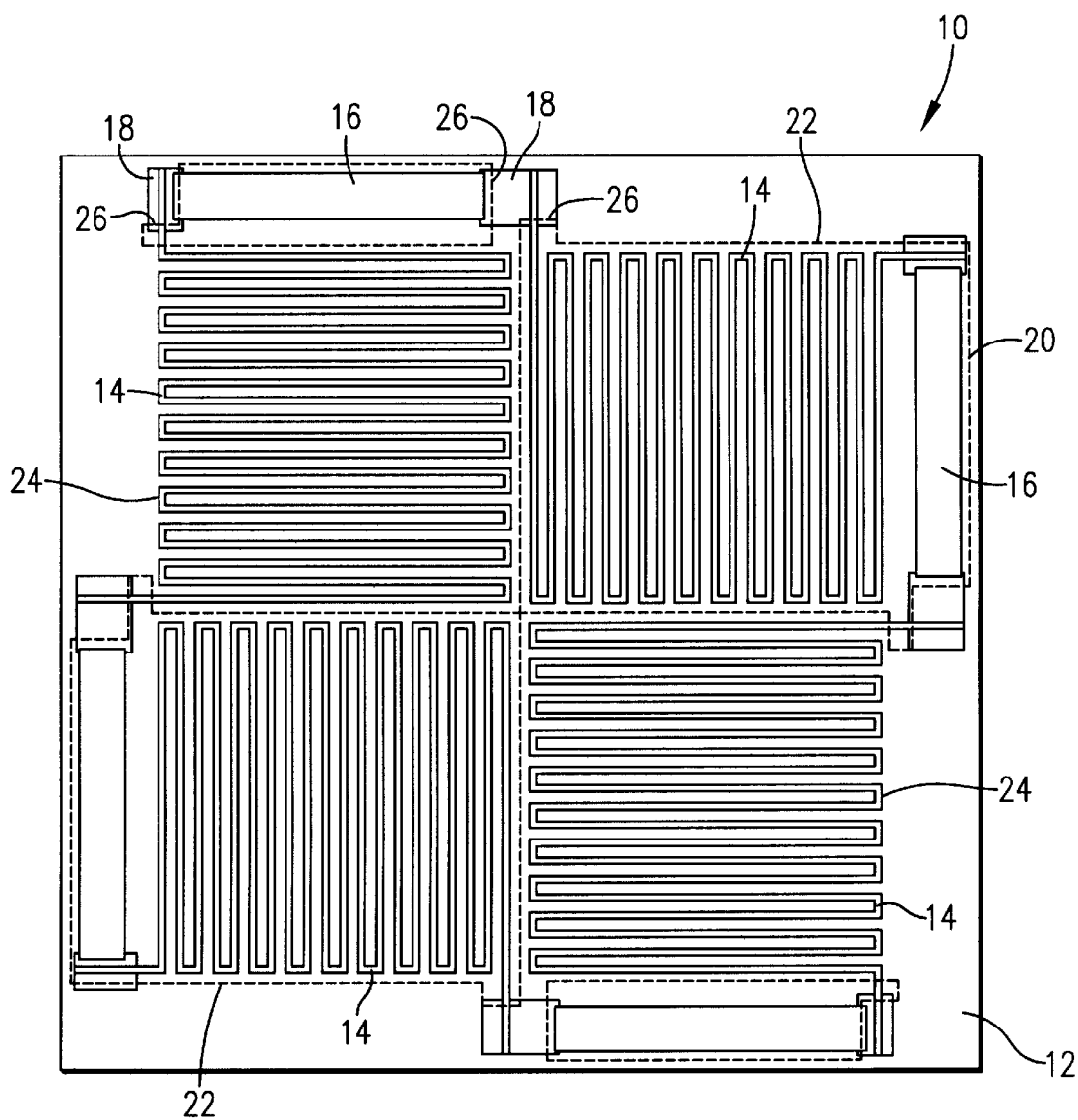
FIG. 1. Plan view of a preferred embodiment of a sensor of the present invention process.

FIG. 1 depicts an overall view of a preferred embodiment of the present invention sensor, which sensor is generally denoted by the numeral 10. This preferred embodiment sensor is mounted upon a suitable nonconductive substrate 12 onto which substrate 12 are formed a plurality of electrically conductive patterns or conductor grids 14. As is generally depicted in FIG. 1, these grids 14 are laid out with a relatively high aspect ratio so as to form a large amount of exposed area per unit resistance of the resulting grids. As is discussed further below, these grids are comprised of palladium material which is sensitive to the presence of hydrogen. Preferably the sensor also comprises a plurality of resistors 16 suitable for trimming so that the electrical resistances in the various conductor grid 14 and resistor 16 combinations can be made equal. At the intersection of the conductor grids 14 and resistors 16 are located solder pads 18 which provide a reliable electrical connection between conductor grid 14 and resistors 16 and, also, form points suitable for soldering conductors to make external connections (not shown; see FIG. 5). Shown on FIG. 1 in dashed outline is an electrically nonconductive, hydrogen impermeable layer of passivation material 20. (In referring to passivation materials as "nonconductive," it is noted that passivation materials typically are slightly electrically conductive, but for the purpose of the present invention, the minimal conductance does not cause a significant difference in the resistance of the passivated grid. As tested, the passivation material produced a shift in the grid resistance of less than 1 percent. Further, the bridge balancing by resistor trimming is preferably performed after passivation.) In the preferred embodiment shown in FIG. 1, the passivation material 20 covers two of the four conductor grids 14, which will be referred to herein as passivated grids 22, and leaves two of the four grids exposed, which will be referred to herein as exposed grids 24. Further, the resistor material 16 preferably is also covered by the passivation layer 20. The passivation material is also preferably utilized to form solder dams 26 at the edge of solder pads 18.

Figure 2:
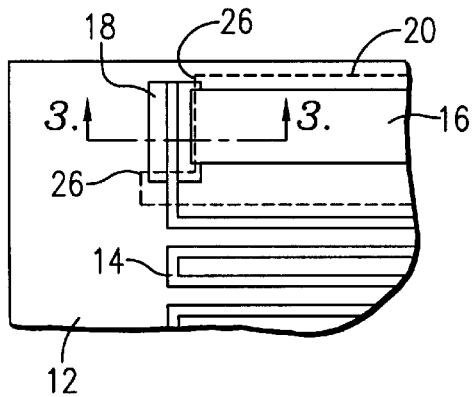
FIG. 2. Detail view of a portion of a present invention sensor, showing details of a resistor and bonding pad.
Figure 3:
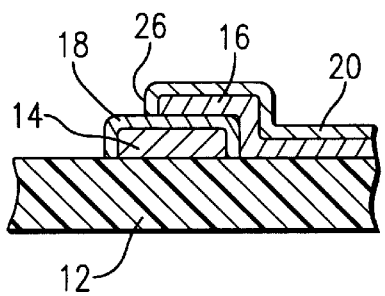
FIG. 3. Section taken along line 3—3 of FIG. 2.

Referring to FIG. 2, these solder dams 26 effectively block the edges of both resistor 16 and conductor grids 14 from exposed solder pad 18. In use, these solder dams help prevent wicking of solder material onto other components of the sensor 10 when external connections (not shown) are made to solder dams 26. FIG. 3 is a section taken through the area of one solder pad 18 showing the relative orientation of a portion of the conductor grids 14 on the substrate which portion is covered by a solder pad 18, to which is connected resistor material 16. This view also shows passivation layer 20 covering resistor 16 and forming solder dam 26.

Figure 4:
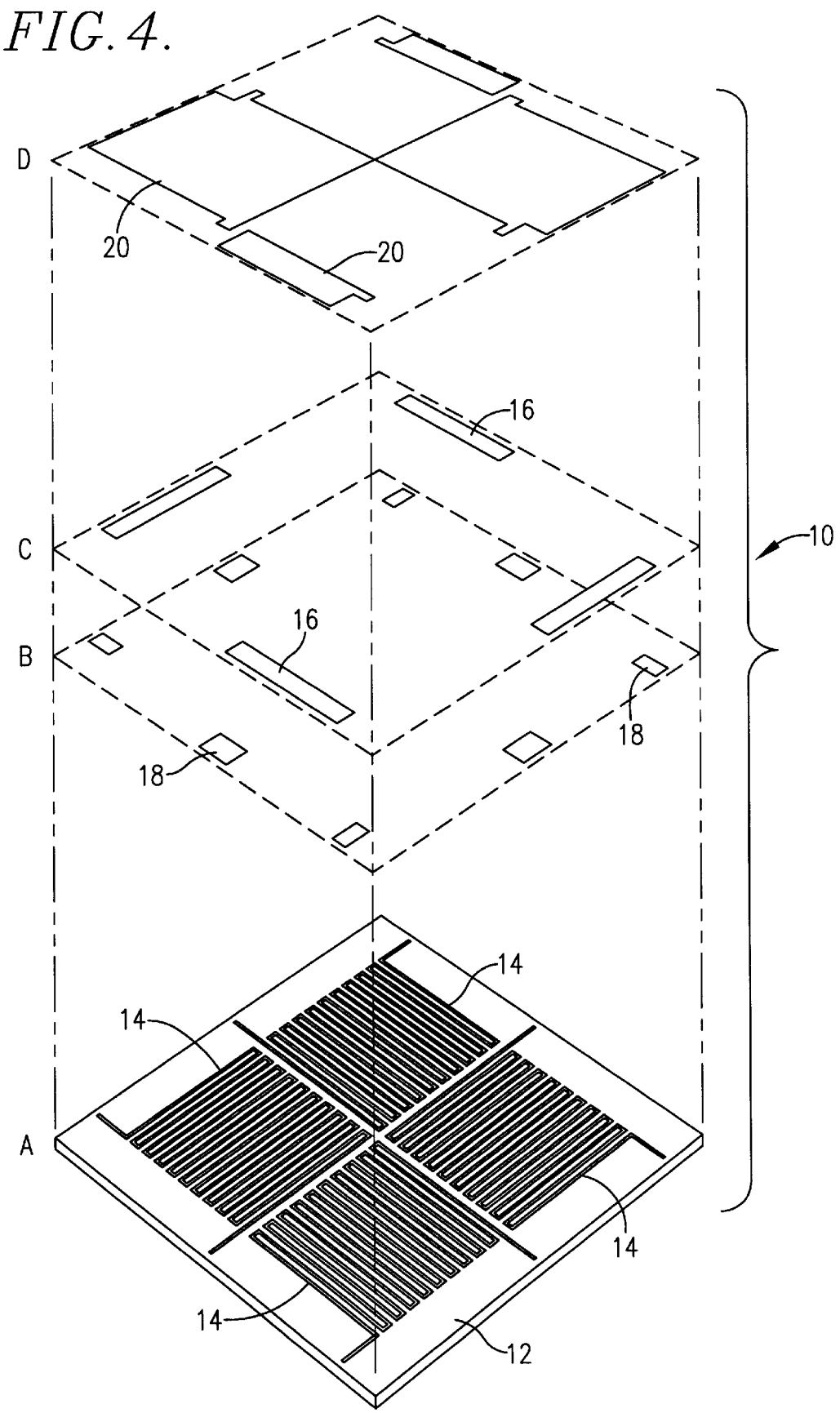
FIG. 4. Exploded view of sensor, showing the preferred sequence of printing layers.

To further explain the layering of materials on this preferred embodiment sensor, FIG. 4 shows an exploded view of a preferred embodiment of the present invention sensor. FIG. 4 shows four levels of layering on the substrate 12. Level denoted "A" shows application of the palladium conductor grid 14 on substrate 12 forming the basic conductor grid pattern. Layer denoted "B" shows layout of solder pads 18 which preferably are applied to the substrate subsequent to application of conductor grids 14. It should be noted that two solder pads 18 per serpentine pattern are shown, which in this example result in a total of eight solder pads 18. As would be known to one skilled in the art, the solder pads 18 are located at each end where connection of further elements is required. Thus, in this application, solder pads 18 are located at each end of the serpentine pattern forming palladium conductor grid 14. Layer "C" shows layout pattern for four resistors 16 to accompany the four conductor grids 14 Each end of resistors 16 is laid out to terminate upon a solder pad 18 and form an electrical connection therebetween. The final layer of the preferred embodiment sensor, layer "D," shows a preferred printing pattern for the passivation layer 20. The passivation layer 20 as shown in FIG. 4 covers two of the four conductor grids 14 as well as all four of the resistors 16, thus forming solder dams 26 at each of the solder pads 18.

Figure 5:
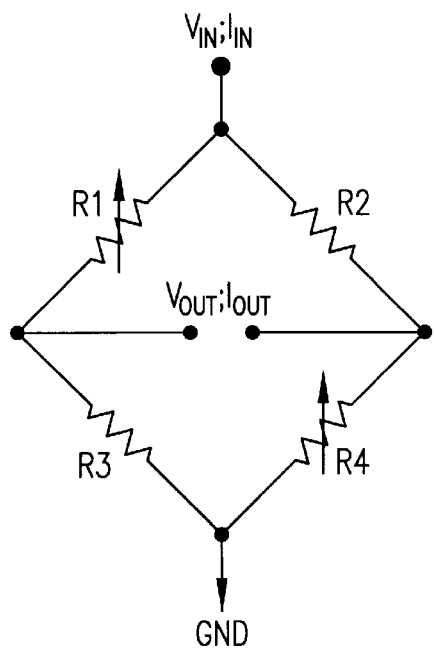
FIG. 5. Circuit diagram of a preferred embodiment of one sensor.

FIG. 5 depicts a standard Wheatstone bridge network. As known to one skilled in the art, a Wheatstone bridge is comprised of four resistors, marked here as R1–R4, configured in a "diamond" pattern forming four nodes. Between two opposite nodes, a voltage producing a current, shown as $I_{in}$ to ground in FIG. 5, is imposed. A current $I_{out}$ (or voltage) may then be measured. As is known to one skilled in the art, if R1×R4=R2×R3, the bridge is considered balanced and the detector current $I_{out}$ will be zero. Typically, Wheatstone bridges are used to determine the resistance value of an unknown resistor by rebalancing the bridge using a precision variable resistance. Similarly, if two of the resistors in question, shown as R1 and R4 are made "variable" the balance of the bridge will be changed and the bridge will be highly sensitive to small changes in those resistances. Applied to the present invention sensor, if resistors R1–R4 are of equal resistance and made of palladium, and if R2 and R3 are encapsulated in a hydrogen impermeable electrically insulative material while resistors R1 and R4 are left exposed, and since the electrical resistance of palladium changes upon exposure to hydrogen gas, the resulting bridge balance changes upon exposure to hydrogen. It should be noted that other types of detector arrangements could be utilized, for example, only one such conductor grid could be left exposed, however the sensitivity of the resulting network is substantially reduced. For that reason, the most preferred embodiment utilizes two of four palladium conductor grids in a Wheatstone bridge arrangement to form the preferred embodiment sensor. The manufacturing process described herein is anticipated to produce acceptable sensors using only two palladium conductor grids, one passivated acting as a reference and one exposed to sense hydrogen. It is also noted that forming palladium conductor grids 14 with resistances which are precisely balanced is obviously difficult. For that reason, trimming resistors items 16 in FIG. 1 are applied in series connection to the conductor grids. These resistors may then be trimmed to equalize the resistances at all legs (i.e., R1–R4) of the grid and thus "zero" the detector signal ($I_{out}$, $V_{out}$=0) at a zero hydrogen level.

Figure 6:
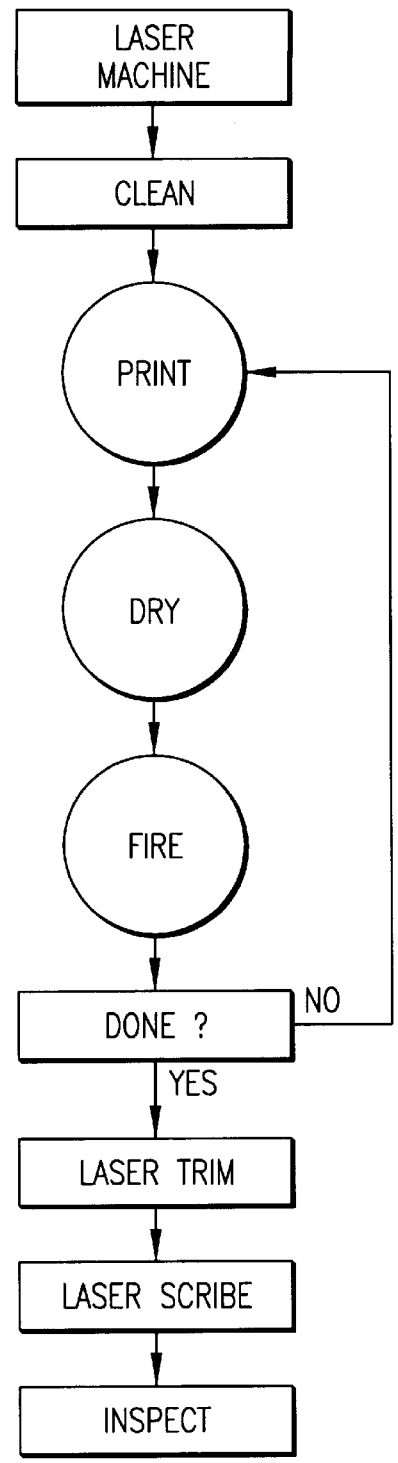
FIG. 6. Flow chart of preferred embodiment of the present invention process of sensor production.

FIG. 6 shows schematically the basic steps necessary in fabrication of a preferred embodiment hydrogen sensor. The first step "laser machine" refers to preparation of a substrate wafer for accurate registration of thick film printing screens as would be known to one skilled in the art. The second step shown "clean" is a further operation to prepare the substrate for various thick film printing operations. The "print, dry, fire sequence" is a typical thick film printing sequence of operations in which a material is printed using techniques known in the art on a substrate, and subsequently dried and fired at an appropriate temperature to achieve the final result. In a preferred embodiment of the present invention process, there are four such "loops" to be performed in forming a sensor, the printing of palladium conductor grids, the printing of solder pads, the printing of resistor material, and the printing of passivation material. However, it can be seen that the process of forming the essential active components of the sensor includes printing of the conductor grid and printing of the passivation material. Subsequent to the printing, drying, and firing of all necessary layers, the trimming resistors are preferably laser trimmed to balance the resistances of the resistor-sensor grid combinations and the resulting wafers are scribed for ease of separation of individual hydrogen sensors. Of course, the final step in any thick film printing operation such as this is inspection of the resulting products.

Substrate 12 is a suitable non-conductive material as is known in the art. One preferred substrate is comprised of a thin flat piece of alumina ceramic. Standard 96% alumina nominally 0.025 inch thick is well-suited to this function. Other substrate materials, such as silicon glass, quartz, mica, other ceramics and porcelain enamel, known in the art can be utilized. The size of the substrate for the completed sensor 10 should be of sufficient size to allow formation of a sufficient area of pattern to produce a sensor with an acceptable output signal. Tests run with a one by one inch nominally sized square sensor provided acceptable results. As is known to one skilled in the art of thick film processing, a substrate is prepared by initially providing index points on the substrate, typically laser machined holes, so that the substrate may be accurately placed beneath repeated screen patterns. In this manner, multiple layers of material may be printed onto the substrate in precise patterns and precise orientation to earlier printed patterns. Preferably, a plurality of sensor systems may be printed on a single substrate for efficiency of manufacture. The index points assist in locating the substrate for scribing and the like to separate multiple individual sensors made on a single chip.

Once the substrate is prepared, screen printing of the various materials and patterns to form the sensors proceeds generally similar to standard thick film printing operations known in the art. However, it has been found that the sequence of printing of the particular materials and the associated firing temperatures of those materials significantly affect the suitability of the resulting sensors for detection of low levels of hydrogen, as well as the repeatability and accuracy of the manufacturing process. In particular, the sequence of material application should provide the same or lower firing temperatures for each successive step, so as to avoid degradation of previously applied layers.

In the preferred embodiment process, the first layer printed onto the prepared substrate 12 is a palladium or conductor paste suitable for thick film printing forming a plurality of palladium conductor grids 14. In a Wheatstone bridge configuration, four palladium conductor grids would be printed forming one leg each of the desired bridge network. A preferred pattern for printing of the palladium conductor grid 14 as shown in FIG. 1 is a serpentine grid pattern designed to provide a large pattern surface area while maintaining reasonably high resistance values, dictating reasonably large aspect ratios. However, limitations in screen printing accuracy and the like limit the fineness of the printed lines and, thus, the aspect ratio. It has been found that an aspect ratio of about 800 squares provides desirable results, although it is expected that a wide range of aspect ratios from about 100 to about 1200 would produce acceptable results. Specific aspect ratios and electrical resistance values are not critical to the practice of this invention and these values can be varied for optimal performance under a given set of parameters. A variety of palladium conductor pastes suitable for thick film printing are commercially available and are generally comprised of palladium, a glass frit binder, and a suitable medium, typically an organic solvent with various resins or the like (reference to palladium conductor paste herein refers to such standard thick film printing pastes containing palladium).

Following the palladium layer, at appropriate locations on the surface of the sensor 10, preferably is printed a standard conductor paste containing suitable conductor material, such as silver, gold, or the like, configured to interconnect the various elements of the sensor, thus forming solder pads 18. (Reference herein to standard conductor paste is to thick film printing compositions containing standard conductor materials, such as silver, gold, and the like). The conductor paste is printed to overlap ends of each of the palladium conductor grids, providing for suitable electrical connections at such points so as to connect to the resistor material subsequently printed thereon. The solder pads thus formed isolate the palladium from degradation due to mixing with subsequent conductor materials printed or soldered on it and facilitate electrical connection of the sensor 10 to an external electronic system to utilize the sensor.

Following the conductor layer, preferably are printed are a set of resistors 16 on the sensor, which resistors are suitable for trimming. Application of a standard resistor compound, e.g., 10 ohms per square, printed on the thick film network allows this balancing to be done.

The final material application step preferably is application (printing) of the passivation material 20. This passivation material 20 must be hydrogen impermeable to block passage of hydrogen gas to protected palladium grids 22, as well as be sufficiently electrically insulating so that the grid will not be shorted. Preferably the passivation material 20 is also mechanically durable to protect the grid and effective to prevent hydrogen passage. Such passivation printing material typically comprises a sintered glass or ceramic in a suitable organic medium.

In the most preferred embodiment, the palladium layer printing was performed with palladium conductor paste E76635-5, as manufactured by DuPont Electronics of Research Triangle Park, N.C., a division of E. I. DuPont deNemours Company of Wilmington, Del., which is a commercially available conductor paste utilizing pure palladium with glass frit, organic binder and solvent. The palladium paste is dried and then fired at a peak firing temperature of about 915° C. plus or minus about 5° C. for about 10.8 minutes plus or minus about 0.8 minutes. (DuPont E76635-5 is generally similar to the composition described in U.S. Pat. No. 5,338,708 (the '708 patent) which is incorporated herein by reference, in that E76635-5 is also a mixture of palladium and glass frit disposed in an organic binder and solvent medium to make a paste. It was found that a pure palladium paste is most preferable for the present invention.) The average fired final thickness was approximately 8 microns. In this embodiment, the second layer printed (the conductor paste for forming solder pads) utilized DuPont product 6120 silver conductor material. (DuPont 6120 contains about 15 parts palladium in 85 parts silver.) Other suitable conductor materials could be printed depending upon the firing temperature and compatibility with the palladium conductor. The DuPont conductor 6120 material is fired at 850° C. plus or minus about 5° C. for 10 minutes plus or minus about a minute. The average fired thickness is about 11 microns. Regarding the third layer, the most preferred resistor material is DuPont product 1711, printed and fired at 850° C. plus or minus about 5° C. for 10 minutes plus or minus about a minute. Other standard 10 ohm/square type resistor inks are anticipated to perform in a similarly acceptable manner to the DuPont 1711. The average dry thickness of this layer desired is about 25 microns. The passivation layer in the most preferred embodiment is performed with a single coating of DuPont 9137 overglaze fired at a peak temperature of 500° C. plus or minus 5° C. for up to one minute. Other glass coating overglaze compounds compatible with the other components of the sensor are anticipated to be acceptable. Note that satisfactory results are expected with as little as essentially zero time at that peak temperature, however oven constraints prevent firing up to a peak temperature at less than some minimal amount of time, here one minute.

One critical feature of the process of the present invention described is that the various material layers are applied so that the peak firing temperature of the first material is the highest peak firing temperature and that similar or lower peak firing temperatures are used on each subsequent layer. In this manner re-flow, cracking, lifting, or other similar damage to earlier layers due to excessive firing temperatures is avoided.

The process of the present invention has been found to reliably produce high quality hydrogen sensors sensitive to levels of hydrogen down to about 1% hydrogen concentration in air or nitrogen.

It should be noted that, as would be apparent to one skilled in the art, various sizes of substrate, grid patterns and the like will produce results similar to those discussed herein.

Certain aspects of the present invention, for example printing multiple materials in an appropriate sequence so that re-firing of these materials occurs at the same or lower temperature with each subsequent re-firing, are essential to the present invention so as to prevent degradation of the earlier printed materials. One skilled in the art would also understand that the Wheatstone bridge approach discussed has distinct advantages to one's ability to detect small changes in the resistivity of the grids involved. However, other patterns would work with various other circuits with a variety of results.

EXAMPLE 1 THICK FILM PROCESSING

Twenty-seven 96% alumina ceramic substrate coupons 0.025 inch thick, were printed with nine sensor patterns each similar to the pattern shown in FIG. 1 (216 total sensors) using palladium conductor paste, DuPont E-76635-5, and standard thick film conductor paste printing procedure known in the art. The parts were dried in a conveyor infrared dryer at a peak temperature of 150° C. for 10 minutes. An average dried thickness of 18 microns was achieved.

The parts were fired in a standard 60-minute cycle conveyor convection oven at a non-standard peak temperature of 915° C. (A firing temperature of 850° C. is considered standard for firing of palladium materials.) An average fired thickness of 8 microns was attained near the center of the serpentine pattern. After firing, it was noticed that the palladium conductors were very porous. Looking at the parts through a microscope at 30× using backlighting, numerous crescent shaped holes were observed. This "lacy" appearance increases the surface area of the conductor pattern and is considered desirable for sensor applications.

Four serpentine patterns were printed per sensor. (Two patterns to be passivated and two left exposed in order to create the Wheatstone Bridge configuration.) The average resistance of the resulting pattern was measured and found to be 95 ohms. The spread of resistances between the serpentine pattern with the highest resistance to the serpentine pattern with the lowest resistance on the same sensor, averaged only 6 ohms. There are 804 squares in each serpentine pattern, so the resistivity of the palladium, processed as described, was about 95,000 mohms/804 squares= 118 mohms/square.

Next a barrier conductor layer was printed over the fired palladium on the pads to receive solder (forming solder pads). The barrier layer keeps the primary (palladium) layer from going into intermetallics and becoming brittle during solder reflow, and this keeps the palladium pads from lifting off the substrate during thermal cycling. The barrier layer was a silver conductor material (DuPont 6120). The silver conductor material was printed and dried in the same way as the palladium conductor material. The average resulting dried thickness for the silver material was 20.1 microns. The barrier layer was fired in a conveyor convection oven at a peak temperature of 850° C. for 10 minutes (60-minute cycle). The silver conductor had an average fired thickness of 11 microns.

Resistor patterns (see FIG. 1, item 16) were printed on 108 sensors (half of the batch) using DuPont 1711 resistor paste. The wet thickness was between 41 and 46 microns. The dry thickness was about 25 microns. Peak firing temperature was 850° C. for 10 minutes based on a 60-minute cycle. The average resistance was 52.617 ohms. After firing, a visual examination of 1711 resistors was conducted and "mud cracking" was observed. This appearance was considered normal for 1711 resistors. Average resistor drift after laser trimming was less than 0.6%.

The passivation layer, DuPont 9137 overglaze, was thinly printed on the entire lot of parts. Peak temperature was 500° C. for one minute. The appearance of the fired overglaze was semi-glossy with no blisters (blisters can allow hydrogen past the passivation layer). If the overglaze is cloudy, it usually means the 9137 was printed too thick or the oven temperature was too low. A glossy appearance with blisters indicates that the temperature was too high or the parts were at temperature too long. Overglaze should be printed over resistors to improve resistor stability after laser trim. The overglaze was not double printed. While printing the passivation layer, solder dams using DuPont 9137 were printed at each pad to receive solder to prevent solder from flowing onto the single layer printed conductor material. Solder dams also assure that the resistance of the serpentine pattern will not be changed by solder flowing onto the neck of the serpentine pattern.

EXAMPLE 2—CHARACTERIZATION OF SENSOR RESISTIVE NETWORKS

Before laser trimming, the resistance values of the serpentine patterns plus their DuPont 1711 resistors fell between 130 and 172 ohms. After laser trimming, 100% of the networks were 175 ohms. That is, every leg of every Wheatstone Bridge was the same. The results of this analysis indicate that the resistive networks on the hydrogen sensor can be trimmed within a tolerance of ±1%. This tolerance includes: the laser trim distribution (the repeatability of the laser to trim resistors to a nominal value), the stability of the resistor (temperature shock, cycle, and 1,000-hour aging), and the accuracy of the bridge used to measure the resistor value. The resulting process yield should be 100% with a ±1% tolerance.

EXAMPLE 3—RESISTOR AGING TESTING

Eighteen hydrogen sensors were removed from a larger lot produced as in Example 1. The resistive elements, printed with DuPont 1711 resistor paste on nine of these networks, were laser trimmed. Each 1711 resistor element, in combination with a grid of DuPont E76635-5 palladium, was laser trimmed to 175 ohms. The resistive elements on the remaining nine networks were not laser trimmed. (These networks were tested along with the trimmed networks. This provides a reference group to determine the effects of laser trimming on stability of the resistors.)

The values of the trimmed resistors were measured and recorded immediately (seconds) after laser trimming. The value of the untrimmed resistors were also measured and recorded. These values were used to calculate the change in resistance due to subsequent testing.

The samples were re-measured again 24 hours later, and the change in resistance was calculated. This was done to obtain some measure of their off-the-shelf stability.

Each sample was then subjected to a solder pot shock test. This test involved placing each test sample individually on molten solder heated to 268° C. for 15 seconds. The sample was removed and placed on a stainless steel table top at 25° C. and allowed to cool. The value of all the resistors was measured, and the change in resistance was calculated.

The networks were then subjected to a temperature cycle test. The test apparatus consisted of two interconnected test chambers. One chamber was set to −50° C. while the other was set to 125° C. A cycle consisted of moving the test samples from one chamber to the other and then back. The approximate transport time was 5 seconds. The networks were held at each temperature a minimum of 15 minutes. The cycle was repeated ten times. Upon completion of this test the resistor values were again measured, and the change from time zero was calculated.

The networks were subjected to the 1,000-hour aging test. The networks were placed in an oven heated to 150° C. At intervals of 200, 600, and 1,000 hours, the networks were removed from the oven and allowed to cool to room temperature. The value of the resistors was measured, and the change compared to time zero was calculated. Table 1 shows the results from the testing. The values shown for both the trimmed and untrimmed resistive elements are the maximum, minimum, and the average for each test.

The tests are listed across the bottom of each chart. The values along the Y-axis represent the percent change in resistance for each test. It can be seen that for this combination of resistive elements that laser trimming does not significantly affect resistor stability. The results for the trimmed and untrimmed networks are very similar.

During the course of this study, the resistive elements printed with the DuPont 1711 resistor paste were viewed under a microscope at approximately 30× magnification. Numerous cracks, spread uniformly across the resistors, were noticed. These cracks were consistent with those typically observed for this paste and are considered normal.

TABLE 1

| Test | Minimum | Maximum | Average |
|---|---|---|---|
| Percent Deviation from Nominal Values - Trimmed Resistors | | | |
| 24 hour | 0 | 0.1 | 0.05 |
| Temperature Shock | −0.05 | −0.15 | −0.07 |
| Temperature cycle | 0.175 | 0.45 | 0.3 |
| 200 hour | −0.1 | 0.1 | 0 |
| 600 hour | 0.5 | 0.95 | 0.72 |
| 1,000 hour | 0.35 | 0.85 | 0.57 |
| Percent Deviation from Nominal Values - Untrimmed Resistor | | | |
| 24 hour | 0 | 0.8 | 0.4 |
| Temperature Shock | −0.06 | −0.28 | −0.15 |
| Temperature cycle | 0.2 | 0.5 | 0.35 |
| 200 hour | 0 | −0.2 | −0.08 |
| 600 hour | 0.55 | 0.89 | 0.74 |
| 1,000 hour | 0.47 | 0.73 | 0.61 |

EXAMPLE 4—PALLADIUM OXIDATION

When the palladium serpentine patterns of Example 1 came out of the furnace, they were even toned and dark gray in color. After being subjected to hydrogen, light gray patches emerged. This effect increased upon more extensive exposure to hydrogen.

The samples were evaluated with a scanning electron microscope evaluation, both the light gray areas and the dark gray areas are essentially palladium metal. Auger microprobe analysis detected only a mono-layer of oxidation on the light gray patches, about 10–30 Å thick but the dark gray areas contain relatively deep layers of oxidation, up to about 5,000 Å thick. Based upon this analysis, it is opined that when the serpentine patterns come through the furnace cool-down zone, they are uniformly oxidized. Upon exposure to hydrogen, the oxidation layer was reduced. Oxidation removal is desirable to make the sensors more responsive.

EXAMPLE 5—HYDROGEN DETECTOR PERFORMANCE TESTING

Performance testing was performed on thick film hydrogen detectors manufactured as described in Example 1. The tests were of hot, cold, and ambient tests in air, and tests at ambient in 3% and 30% hydrogen in nitrogen. The sensors were wired together in a set of ten sensors.

Data was collected from each sensor set under computer control. The data collected from the sensors was in the form of voltage measurements. Each sensor Wheatstone bridge network had five volts of power applied during testing; the data collected was the measurement of the voltage between the two legs of the network (Vout in FIG. 5).

All temperature tests were performed in air; the purpose of these tests was to test sensor stability at temperature. Gas tests were performed in a quart jar where the sensor sets could be exposed to a hydrogen environment. The hydrogen gas mixture flowed into the jar across the sensors and out through a vent to the open atmosphere. The following table summarizes the data acquired for the various tests conducted.

TABLE 2

| Test Temperature | Test Atmosphere | Test Results |
|---|---|---|
| Ambient | Air | The network outputs (Vout) varied slightly (microvolts). |
| 20, 0, −10, −20, −30, −40° C. dwelled at each temp 15 min. | Air | The network outputs (Vout) varied slightly with the offset following temperature. The total Vout variance between high and low temperature was about 1–millivolts. |
| 25, 35, 45, 55, 65, 75° C dwelled at each temp 10 min. | Air | Outputs (Vout) varied slightly with the offset following temperature. The total Vout variance between high and low temperature was about 1–3 millivolts. |
| Ambient | 30% H in Nitrogen | The sensors took about 3 min. to react to the hydrogen and then the sensors saturated (peaked and maintained) immediately with a Vout of 33–42 millivolts. The recovery to pre-hydrogen exposure took many hours and the sensors did not fully recover but, rather, displayed a residual Vout of 5–8 mv). |

TABLE 2-continued

| Test Temperature | Test Atmosphere | Test Results |
| --- | --- | --- |
| Ambient | 3% H in Nitrogen | The sensors took about 6 min. to react; saturation occurred at 75 min. (about 28–41 mv). The sensors displayed the same recovery time and the same residual offset as above at 30% hydrogen. |
| Ambient | 3% H in Nitrogen | The sensors were allowed to saturate then, heat (about 70° C.) was applied to aid recovery. Recovery was immediate; however, a residual offset remained. |

(Note that because of the testing procedures used, these results are considered qualitatively representative of the performance of the sensors, but is not deemed quantitatively precise).

The sensors showed good stability in temperature testing, which means any significant changes in the balance of the two resistor legs would be due to the presence of hydrogen.

The relation between the measured voltage and change in resistance of the palladium grids can be calculated as follows, assuming Iout is negligible (refer to FIG. 5):

$$\text{If } V_{out} = V_{in}\left(\frac{R3}{R1+R3} - \frac{R4}{R2+R4}\right),$$

R2=R3=R and
R1=R4=R+Rdel where R is the initial value of the grids and Rdel is the change in resistance due to the presence of hydrogen gas;

$$\text{then } V_{out} = V_{in}\left(\frac{R}{R+R+Rdel} - \frac{R+Rdel}{R+R+Rdel}\right)$$

$$\text{which reduces to } V_{out} = V_{in}\frac{Rdel}{2R+Rdel}$$

Given a 5 volt Vin, a 0.04 volt Vout at 30% hydrogen gas concentration and a 175 ohm R value, Rdel is 2.8 ohms.

The reaction time for the sensor to detect hydrogen (that is, cause a voltage between the legs to increase) was at first 3–6 minutes. In subsequent tests, the initial reaction time decreased to 15–30 seconds, this is due to an oxidation film on the surface of the sensors; this oxidation was eroded as they were tested in hydrogen environments, and as a result, the sensitivity of the sensor increased. The time to saturation (in 3% hydrogen) also decreased from about 75 minutes down to about 15 minutes. The saturation time for 30% hydrogen was typically less than two minutes. It was noted that the sensors began to react to the presence of hydrogen as soon as hydrogen was introduced into the testing chamber, displacing the pure nitrogen in it. Based upon observation of the sensors reaction, it was considered that the sensors reliably will detect hydrogen beginning at or below a 1% hydrogen gas concentration in a carrier gas such as nitrogen or air. Further, based upon experience with other palladium sensors, the present invention should also be suitable to detect low levels of hydrogen in liquids, such as electrical transformer oil.

The foregoing embodiments and descriptions have been described for illustrative purposes only. Numerous changes, modifications, and alternatives may be made without departing from the spirit and scope of the invention. The scope of this invention is limited only by the following claims.

I claim:

1. A thick film process to manufacture hydrogen sensors comprising:
    printing a palladium paste onto an essentially inert, electrically nonconductive substrate in a pattern to form at least two electrical networks;
    firing said substrate and palladium paste to firmly adhere said electrical networks to said substrate;
    printing a standard conductor paste onto said substrate at ends of said electrical networks to form pads;
    firing said substrate and standard conductor paste to firmly adhere said pads to said substrate;
    printing a barrier material over the pads to form a barrier layer on the pads;
    firing said substrate and barrier material to firmly adhere the barrier layer to the pads;
    printing a passivating material which is essentially inert, and hydrogen impermeable, onto at least one, but less than all said electrical networks; and
    firing said substrate and passivating material to firmly adhere said passivating material to said electrical networks, without forming bubbles, voids or cracks.

2. The process as claimed in claim 1 wherein there are four said electrical networks and said networks are connected in a Wheatstone bridge configuration.

3. The process as claimed in claim 1 further comprising the following steps between the steps of firing said barrier material and printing said passivating material:
    printing a resistor paste to form a resistor pattern on said nonconductive substrate so as to form resistor patterns between adjacent electrical networks;
    firing said substrate and resistor paste to firmly adhere said resistor patterns to said substrate without forming bubbles, voids or cracks.

4. The process claimed in claim 3 in which said pattern for said electrical networks is a serpentine pattern with an aspect ratio of about 800.

5. The process as claimed in claim 3 wherein said palladium paste is type E76635-5 as manufactured by DuPont Company; said first firing temperature is from about 910 to about 920° C.; and said first duration is from about 10.0 to about 11.6 minutes.

6. The process as claimed in claim 3 wherein said conductor paste is DuPont type 6120 and said third firing temperature is from about 845 to about 855° C. and said third duration is from about nine to about eleven minutes.

7. The process as claimed in claim 3 wherein said resistor paste is DuPont type 1711 and said fourth firing temperature is from about 845 to about 855° C. and said fourth duration is from about nine to about 11 minutes.

8. The process as claimed in claim 3 wherein said passivation material is DuPont 9137 and said second firing temperature is from about 495 to about 505° C. and said second duration is from about zero to about one minute.

9. The process claimed in claim 3 wherein said pattern for said electrical networks is a serpentine pattern with an aspect ratio of about 800; wherein said palladium paste is type E76635-5 as manufactured by DuPont Company, said first firing temperature is from about 910 to about 920° C., and said first duration is from about 10.0 to about 11.6 minutes; wherein said standard conductor paste is DuPont type 6120 and said third firing temperature is from about 845 to about 855° C., and said third duration is from about nine to about eleven minutes; wherein said resistor paste is DuPont type 1711, said fourth firing temperature is from about 845 to about 855° C. and said fourth duration is from about nine to about 11 minutes; wherein said passivation material is DuPont 9137, said second firing temperature is from about 495 to about 505° C., and said second duration is from about zero to about one minute.

10. A thick film process to manufacture hydrogen sensors comprising the following steps in the order presented:
   (a) printing a palladium conductor paste consisting essentially of pure palladium, glass frit, organic binder and a solvent, onto an essentially inert, electrically nonconductive substrate in a pattern to form four electrical networks; each of said networks is arranged in a serpentine configuration so as to produce an aspect ratio of from about 100 to about 1200;
   (b) firing said substrate and palladium conductor paste at a first peak temperature and for a first duration, which temperature and duration are sufficient to firmly adhere said electrical networks to said substrate;
   (c) after steps (a) and (b), printing a standard conductor paste to form pads on said substrate at ends of said electrical networks;
   (d) firing said substrate and standard conductor paste at a second peak temperature and for a second duration, which temperature and duration are sufficient to firmly adhere said pads to said substrate, said second temperature being less than or equal to said first temperature;
   (e) printing a resistor paste to form a resistor pattern suitable for trimming on said substrate so as to form resistor patterns adjacent said electrical networks;
   (f) firing said substrate and resistor paste at a third peak temperature and for a third duration, which temperature and duration are sufficient to firmly adhere said resistor patterns to said substrate, said third temperature being less than or equal to said second temperature;
   (g) printing a passivating material which is essentially inert, essentially nonconductive, and hydrogen impermeable, onto two of said electrical networks; and
   (h) firing said substrate and passivating material at a fourth peak temperature and for a fourth duration, which fourth temperature and fourth duration are sufficient to firmly adhere said passivating material, said fourth temperature being less than or equal to said third temperature.

11. The process as set forth in claim 10 further comprising the following steps between steps (d) and (e):
   printing a barrier material over the pads to form a barrier layer on the pads; and
   firing said substrate and barrier material to firmly adhere the barrier layer to the pads.

12. The process as set forth in claim 10, further comprising the step of printing a passivating material at the edge of each of the pads to form solder dams to block the edges of the pads from the electrical networks and the resistor patterns to prevent wicking of solder material onto the electrical networks and the resistor patterns.

* * * * *